United States Patent [19]

Pucci et al.

[11] Patent Number: 5,158,652
[45] Date of Patent: Oct. 27, 1992

[54] PROCESS FOR THE SEPARATION OF TERT. BUTYL ETHYL ETHER FROM MIXTURES

[75] Inventors: Annick Pucci, Croissy sur Seine; Paul Mikitenko, Noisy le Roi; Massimo Zuliani, Rueil Malmaison, all of France

[73] Assignee: Institut Francais du Petrole, Rueil-Malmaison, France

[21] Appl. No.: 682,289

[22] Filed: Apr. 9, 1991

[30] Foreign Application Priority Data

Jan. 30, 1991 [FR] France .................. 91 01132

[51] Int. Cl.$^5$ .......................... B01D 3/14; C07C 41/42
[52] U.S. Cl. ........................................ 203/73; 203/75; 203/77; 203/78; 203/80; 203/88; 203/DIG. 6; 568/697; 568/699; 568/913
[58] Field of Search .................... 203/73, 74, 75, 77, 203/78, 80, 82, 84, 88, DIG. 6; 568/699, 697, 913

[56] References Cited

U.S. PATENT DOCUMENTS

| | | | |
|---|---|---|---|
| 2,721,222 | 10/1955 | Cottle et al. | 568/699 |
| 4,322,565 | 3/1982 | Dotson et al. | 568/699 |
| 4,334,890 | 6/1982 | Kochar et al. | 568/697 |
| 4,440,963 | 4/1984 | Childs | 568/699 |
| 4,504,687 | 3/1985 | Jones | 203/DIG. 6 |
| 5,015,783 | 5/1991 | Vora et al. | 568/697 |

*Primary Examiner*—Wilbur Bascomb, Jr.
*Attorney, Agent, or Firm*—Millen, White & Zelano

[57] ABSTRACT

For the separation of tert. butyl ethyl ether from mixtures with ethanol, there are provided two distillation stages, the first being carried out at a pressure $p_1$ equal to or higher than 1 bar, the second at a pressure $p_2$ below $p_1$ by a value $\Delta p$ or 0.5 to 12 bars, $p_2$ then being 0.5 to 10 bars. The second column distillate is partly supplied as reflux to the head of the second column and is in part recycled to the head of the first column. The purified TBEE is collected at the bottom of the first column and the purified ethanol at the bottom of the second column.

This separation process can be integrated into a TBEE production unit comprising etherification by ethanol of the isobutylene contained in a $C_4$ fraction from a catalytic cracking or steam cracking stage. The ethanol separated from the TBEE is then recycled to the etherification zone.

13 Claims, 1 Drawing Sheet

PROCESS FOR THE SEPARATION OF TERT. BUTYL ETHYL ETHER FROM MIXTURES

BACKGROUND OF THE INVENTION

The invention relates to the production of tert. butyl ethyl ether (TBEE).

It is known that tert. butyl ethyl ether, like tert. butyl methyl ether (TBME), can be used as a high octane rating additive for reduced lead or lead-free gasoline TBEE can be added to gasoline in concentrations ranging e.g. up to approximately 15% by volume.

One process for the production of TBME consists of carrying out a reaction of adding methanol to isobutylene, e.g. contained in a $C_4$ fraction from a catalytic cracking or steam cracking stage. After reaction, the residual methanol is generally separated by azeotropic distillation with the $C_4$ hydrocarbons, which makes it possible to obtain in a relatively easy manner the TBME with an appropriate level of purity for adding to gasoline.

The production of TBEE can be carried out by an identical process, where the methanol is replaced by ethanol. Such a process is e.g. described in "ETBE, un avenir pour l'éthanol" by A. Forestiere, B. Torck and G. Pluche, communication at the Conference on the Biomass for Energy and Industry, Lisbon, Oct. 9-13 1989 and "MTBE/ETBE, an Incentive Flexibility for Refiners" by A. Forestiere et al, communication at the Conference on Oxygenated Fuels in Europe, London May 22/23 1990.

However, in such a process and unlike in the case of TBME, after the elimination of the $C_4$ hydrocarbons, almost all the residual ethanol is mixed with the TBEE produced. The existence of an ethanol-TBEE azeotrope with 21% by weight ethanol at atmospheric pressure and boiling at 66.6° C. makes it difficult to separate the TBEE with a level of purity adequate for satisfying specifications regarding the ethanol content in gasoline. Thus, the ethanol content of TBEE must generally be between 0.5 and 10% by weight. Advantageously, the TBEE must be purified to less than 2% by weight ethanol in order to be transferred to the refinery.

SUMMARY OF THE INVENTION

Thus, in order that TBEE can compete with TBME as an additive improving the octane rating of lead-free gasoline it is particularly desirable to find an economically attractive separation process and this is what the invention proposes.

The invention therefore relates to a process for the separation of TBEE from mixtures which it forms with ethanol and more particularly from TBEE-ethanol mixtures resulting from the reaction of ethanol with a steam or catalytic cracking $C_4$ fraction.

The invention also relates to a process for the production of TBEE including such a separation operation and in which the ethanol is recycled to the etherification reactor.

The TBEE separation process according to the invention more generally applies to mixtures essentially constituted by ethanol and TBEE in varied proportions and more particularly to mixtures resulting from the reaction of adding ethanol to the isobutylene contained in a steam or catalytic cracking $C_4$ fraction and which generally contain approximately 5 to 50 and usually 10 to 30% by weight ethanol. They can also contain small proportions of other constituents, essentially dimers of isobutylene, such as trimethyl pentenes, tertiary butyl alcohol, diethylether and $C_5$ hydrocarbons.

BRIEF DESCRIPTION OF THE DRAWING

The TBEE separation process according to the invention and which involves two successive distillations at different pressures is described in greater detail relative to the attached schematic flow sheet in FIG. 1. The pressures indicated in the present description are absolute pressures and are expressed in bars (1 bar=0.1 MPa).

DETAILED DESCRIPTION OF THE DRAWING

Figure 1:
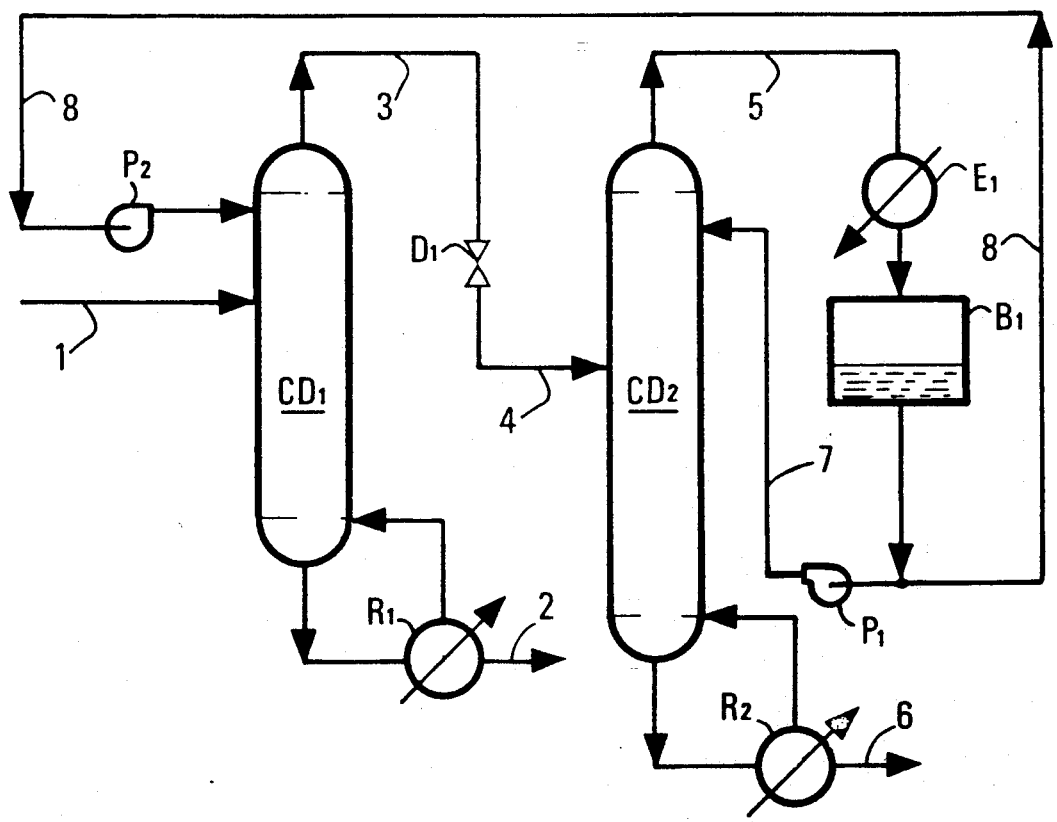

The charge consisting of the mixture containing the ethanol and the TBEE to be separated is supplied by the line 1 to a first distillation column $CD_1$ under a pressure $p_1$ equal to or higher than 1 bar and e.g. 2.5 to 15 bars. Heated by a reboiler $R_1$, said column operates between a bottom temperature generally between 78° and 180° C. and a head temperature generally ranging between 67° and 160° C. The charge is preferably introduced at the bubble point at the considered pressure and at the tray having the composition as close as possible to that of said charge, e.g. in the upper part of the column for compositions close to 20% by weight ethanol (which, in the production of TBEE, correspond to a large ethanol excess compared with the isobutylene quantity present at the inlet or intake of the etherification reactor). The residue of the distillation passing out of the bottom of the column through line 2 is constituted by purified TBEE.

At the head of the column, the distillate leaving by line 3 has a composition close to the composition of the azeotrope at pressure $p_1$. For example, for a pressure $p_1$ of 5 bars, the composition of the distillate is close to 30% by weight ethanol for 70% by weight TBEE.

This distillate is expanded in the relief valve $D_1$ to a pressure $p_2$, which is generally below the pressure $p_1$ by a value $\Delta p$ of 0.5 to 12 bars and more particularly 2 to 10 bars, $p_2$ then generally being 0.5 to 10 bars. After expansion, the distillate is introduced by the line 4 into the upper part of a second distillation column $CD_2$ operating at the pressure $p_2$. Heated by the reboiler $R_2$, said column operates between a bottom temperature between 60° and 150° C. and a head temperature generally between 50° and 130° C.

At the head of the column $CD_2$ is recovered by the line 5 a distillate having a composition close to the azeotrope under the pressure $p_2$ and therefore containing an ethanol proportion below that of the feed (first column distillate). For a pressure $p_2$ of 1 bar, the composition of the distillate can be approximately 21% by weight ethanol and 79% by weight TBEE. A residue constituted by purified ethanol is recovered by line 6 at the bottom of the column.

The distillate leaving by the line 5 is supplied to a heat exchanger $E_1$, where it gives off the heat on condensing. The liquid is collected in the round-bottomed flask $B_1$. From the latter part of the liquid is pumped by the pump $P_1$ and is supplied by the line 7 to the head of the column $CD_2$, where it acts as reflux. The liquid proportion supplied in this way is determined as a function of the purity which it is wished to achieve for the ethanol collected at the bottom of the column. The remainder of the liquid is recycled by the line 8 and the pump $P_2$ to the head of the first column $CD_1$, where it serves as liquid reflux.

As a function of the operating conditions used, the TBEE obtained as residue at the bottom of the first column can have a degree of purity of at least 98 molar % (i.e. at least approximately 99% by weight).

It is possible to adjust the operating conditions in such a way as to obtain a product with a further reduced ethanol content, e.g. as low as 1000 ppm in moles. The purity of the TBEE then reaches 99.95% by weight.

The degree of purity of the TBEE obtained more particularly depends on the reflux used at the head of column $CD_1$ comprising on the one hand the recycling of the distillate of column $CD_2$ by the line 8 and on the other hand a possible liquid reflux from the head vapors of the line 3, said possible reflux not being shown in FIG. 1.

The second column residue can have an ethanol content of at least 96 molar % (i.e. at least approximately 92% by weight).

It is also possible to adjust the operating conditions in such a way that the product contains as little as 1000 ppm in moles of TBEE. The purity of the ethanol then reaches 99.8% by weight.

Among the impurities possibly contained in the charge to be treated by the separation process according to the invention, the dimers of isobutylene (i.e. essentially trimethyl pentenes) are collected with the TBEE at the bottom of the first column. The tert. butyl alcohol is collected with the ethanol at the bottom of the second column. The diethyl ether and the $C_5$ hydrocarbons pass out at the head of the first column. They do not affect either the operating temperatures, or the purity of the TBEE produced.

The process according to the invention has the advantage of great simplicity and reduced energy costs. Thus, the thermal energy costs for treating a charge containing e.g. 80% by weight TBEE and 20% by weight ethanol does not generally exceed 600 kcal/kg of treated charge for products obtained with purity levels of 99.9 molor %.

The inventive TBEE separation process as described hereinbefore can advantageously be integrated into a complete TBEE production process by etherification using ethanol of the isobutylene contained in a catalytic or steam cracking $C_4$ fraction.

Figure 2:
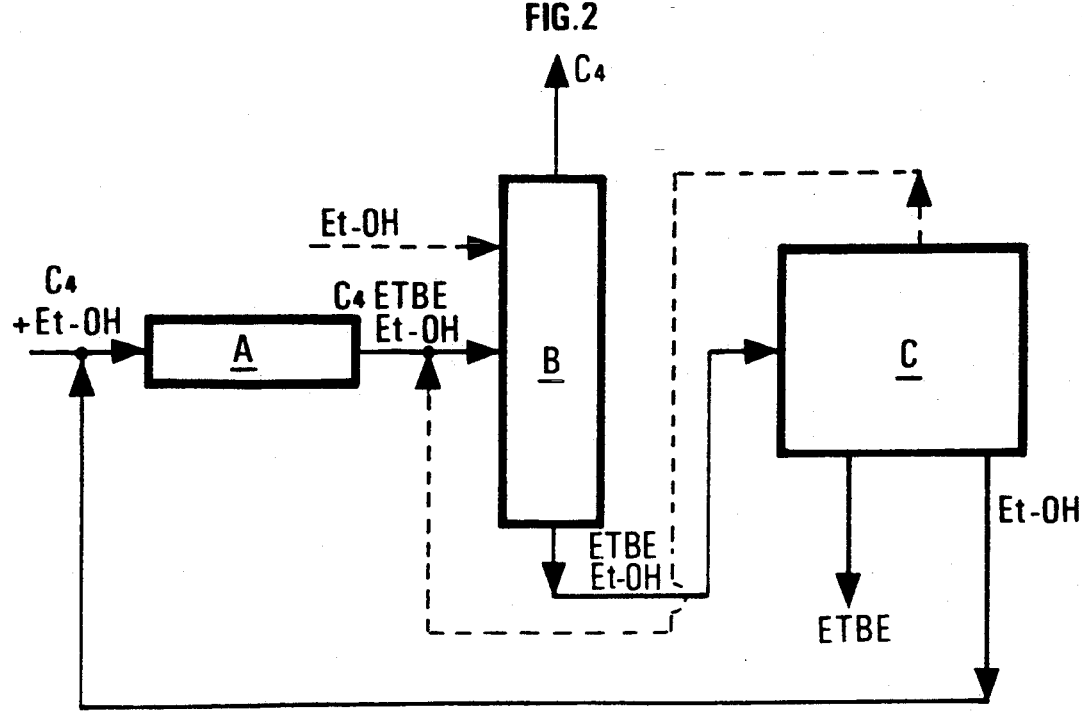

The TBEE production process described in conjunction with the attached FIG. 2 then comprises the following stages: in a zone A, contacting takes place, under reaction conditions, between ethanol and a catalytic or steam cracking $C_4$ fraction; the product from the reaction zone A mainly contains TBEE, ethanol, $C_4$ hydrocarbons other than isobutylene and as impurities isobutylene which has not reacted, dimers of isobutylene (essentially trimethyl pentenes), tert. butyl alcohol, diethyl ether and $C_5$ hydrocarbons (pentanes and pentenes) already contained in the initial $C_4$ fraction. This product is supplied to a distillation zone B, where separation takes place at the head of the highly isobutylene-depleted $C_4$ hydrocarbons and at the bottom of a mixture of TBEE and ethanol containing the other impurities. If a more complete isobutylene elimination is desired, in place of a simple distillation B, it is possible to carry out a reactive distillation B' involving a topping up with ethanol, in the manner indicated in dotted line form in FIG. 2. In all cases, the mixture of TBEE and ethanol collected at the bottom of zone B is fed into a zone C, where the separation process of the invention is carried out.

It is of particular interest to note that, in general, following the treatment performed in zone B, the mixture mainly containing TBEE and ethanol is obtained under an adequate pressure to permit direct introduction into the first distillation column of the separation zone C. From zone C, the purified ethanol collected is advantageously recycled as a top-up product to the reaction zone A and/or to the reactive distillation zone B'.

In addition, the light impurities consisting of traces of diethyl ether and $C_5$ hydrocarbons can be eliminated by a purge carried out at the head of the first column or at the head of the second column and can be recycled to the intake of the distillation zone B, as is diagrammatically indicated in dotted line form in FIG. 2. As stated hereinbefore, among the impurities, the dimers of isobutylene are collected with TBEE and tert. butyl alcohol with ethanol.

The following examples illustrates the invention.

EXAMPLE 1

The separation of a TBEE-ethanol mixture is carried out in such a way as to obtain TBEE with a degree of purity of approximately 99% by weight.

The charge is constituted by 80% by weight TBEE and 20% by weight ethanol. It is introduced on the sixth tray under 5 bars, at 119° C. and with a flow rate of 1.5 kg/hour in a first distillation column operating at 5 bars. This diameter 5 cm stainless steel column has 16 overflow perforated trays spaced by 5 cm.

It is equipped with an electrically heated boiler. The entire column is thermally insulated so as to avoid heat losses. The column temperature is between 132° C. at the bottom and 118° C. at the head.

The distillate containing 32% by weight ethanol and 68% by weight TBEE is expanded to 1 bar. Under a flow rate of 3.39 kg/hour, it is supplied to the sixth tray of a second column operating under 1 bar. The second column is an adiabatic, diameter 50 mm, glass column having 20 overflow perforated trays, equipped with an electrically heated boiler, a water condenser and a reflux round-bottomed flask. The column temperature is between 75° C. at the bottom and 67° C. at the head.

The distillate containing 74% by weight TBEE and 26% by weight ethanol is condensed. A fraction of the condensate is passed under a flow rate of 3.69 kg/hour to the head of the second column as reflux. The remainder of the condensate is recycled at a rate of 3.07 kg/hour to the head of the first column.

At the bottom of the first column and at a rate of 1.18 kg/hour is collected a product containing 99.1% by weight TBEE and 0.9% by weight ethanol and at the bottom of the second column and with a rate of 0.314 kg/hour is collected a product containing 93.6% by weight ethanol and 6.4% by weight TBEE.

The process used in this example requires an additional energy supply of approximately 450 kcal/h to the reboiler $R_1$ and approximately 180 kcal/h to the reboiler $R_2$.

EXAMPLE 2

A TBEE—ethanol mixture is separated in such a way as to obtain each of the two constituents with a residual content in the other of approximately 1000 ppm in moles.

The same charge as in Example 1 is introduced under a flow rate of 1.5 kg/hour into the first distillation column, equipped with 30 trays and under a pressure of 5 bars, which operates between a bottom temperature of 135° C. and a head temperature of 118° C.

The distillate containing 70% by weight TBEE and 30% by weight ethanol, after expansion to 1 bar, is supplied under a flow rate of 3.93 kg/hour to the second column operating under 1 bar. The temperature of the latter is between 78° C. at the bottom and 67° C. at the head.

The distillate, which contains 75% by weight TBEE and 25% by weight ethanol is condensed. A fraction of the condensate is supplied to the head of the second column under a rate of 4.35 kg/hour and the remainder is recycled at a rate of 3.63 kg/hour to the head of the first column.

At the bottom of the first column and under a flow rate of 1.2 kg/h is collected a product containing 99.95% by weight TBEE and 0.05% by weight ethanol and at the bottom of the second column and at a rate of 0.3 kg/h is collected a product containing 99.8% by weight ethanol and 0.2% by weight TBEE.

The process carried out in this example requires an additional energy supply of approximately 510 kcal/h to the first reboiler $R_1$ and approximately 330 kcal/h to the second reboiler $R_2$.

What is claimed is:

1. A process for the separation of tert. butyl ethyl ether (TBEE) from mixtures thereof with ethanol, said mixtures, upon distillation form azeotropes of the tert. butyl ethyl ether and the ethanol which azeotropes have pressure-dependent compositions, said process comprising:
   a) introducing a charge essentially constituted by a mixture of tert. butyl ethyl ether and ethanol into a first distillation column operating under a pressure $p_1$ equal to or higher than 1 bar and at a temperature ranging between a bottoms temperature of 78° to 180° C. and a head temperature of 67° to 160° C.,
   b) expanding resultant distillate leaving the head of said first column, said distillate having a composition close to that of the azeotrope at said pressure $p_1$ to a pressure $p_2$ of 0.5 to 10 bars and lower than $p_1$ by a value $\Delta p$ of 0.5 to 12 bars, before introducing said distillate into a second distillation column operating at said pressure $p_2$ and at a temperature ranging between a bottoms temperature of 60° to 150° C. and a head temperature of 50° to 130° C.,
   c) condensing resultant distillate leaving the head of said second column, said distillate having a composition close to the composition of the azeotrope at said pressure $p_2$, and partly supplying resultant condensate to the head of the second column and partly recycling said condensate to the head of the first column,
   d) collecting resultant purified TBEE at the bottom of the first column, and
   e) collecting purified ethanol at the bottom of the second column.

2. A process according to claim 1, wherein the charge comprises 5 to 50% by weight ethanol.

3. A process according to claim 1, wherein the charge comprises 10 to 30% by weight ethanol.

4. A process according to claim 1, wherein the pressure $p_1$ is 2.5 to 15 bars and the pressure $p_2$ is lower than the pressure $p_1$ by a value $\Delta p$ of 2 to 10 bars.

5. A process according to claim 1, wherein the charge results from a production of TBEE by etherification with ethanol of isobutylene contained in a $C_4$ fraction from a steam or catalytic cracking stage and said charge contains, apart from TBEE and ethanol, very small proportions of dimers of isobutylene, tert. butyl alcohol, diethyl ether and $C_5$ hydrocarbons, said isobutylene dimers being collected at the bottom of the first column mixed with TBEE, the said tert. butyl alcohol being collected at the bottom of the second column mixed with ethanol, said diethyl ether and said $C_5$ hydrocarbons passing out of the head of the first column.

6. A process according to claim 5, wherein the charge contains approximately 80% by weight TBEE and approximately 20% by weight ethanol.

7. A process for the production of tert. butyl ethyl ether (TBEE) by etherification with ethanol of isobutylene contained in a $C_4$ fraction from a catalytic or steam cracking stage, in which, in a reaction zone A, contacting takes place, under reaction conditions, between ethanol and said $C_4$ fraction, whereby the product from said reaction zone A mainly containing TBEE, ethanol, $C_4$ hydrocarbons other than isobutylene and, as impurities, unreacted isobutylene, isobutylene dimers, tert. butyl alcohol, diethyl ether and $C_5$ hydrocarbons is supplied to a distillation zone B having a head zone and a bottom zone, in which are separated, at the head zone, the $C_4$ hydrocarbons including the unreacted isobutylene, and at the bottom zone, a mixture of TBEE, ethanol and other impurities, and said mixture is supplied to a separation zone C, wherein said mixture is separated in said separation zone C in accordance with the process of claim 1.

8. A process according to claim 7, wherein the purified ethanol from the separation zone C is recycled to the reaction zone A.

9. A process according to claim 7, wherein in order to remove traces of diethylether and hydrocarbon, a purge is carried out on the distillate of the first column or on the distillate of the second column of the separation zone C, resultant purge stream being recycled to the distillation zone B.

10. A process for the production of tert. butyl ethyl ether (TBEE) by etherification with ethanol of isobutylene contained in a $C_4$ fraction catalytic or steam cracking stage, in which, in a reaction zone A, contacting takes place, under reaction conditions, between ethanol and said $C_4$ fraction, whereby the product from said reaction zone A mainly containing TBEE, ethanol, $C_4$ hydrocarbons other than isobutylene and, as impurities, unreacted isobutylene, isobutylene dimers, tert. butyl alcohol, diethyl ether and $C_5$ hydrocarbons is supplied to a reactive distillation zone B' having a head zone and a bottom zone, ethanol is introduced for eliminating unreacted isobutylene and forming additional ethyl tert. butyl ether, in which reactive distillation zone are separated, at the head zone, the $C_4$ hydrocarbons and any residual unreacted isobutylene, and at the bottom zone, a mixture of TBEE, ethanol and other impurities, and said mixture is supplied to a separation zone C, wherein said mixture is separated in said separation zone C in accordance with the process of claim 1.

11. A process according to claim 10, wherein the purified ethanol from the separation zone C is recycled to the distillation zone B'.

12. In a process for the separation of tert. butyl ethyl ether from mixtures thereof with ethanol, said mixtures, upon distillation, forming azeotropes of the tert. butyl ethyl ether and the ethanol, which azeotropes have pressure-dependent compositions, the steps comprising:
   a) introducing a charge essentially constituted by a mixture of tert. butyl ethyl ether and ethanol into a first distillation column operating under a pressure $p_1$ equal to or higher than 1 bar and at a temperature ranging between a bottoms temperature of 78° to 180° C. and a head temperature of 67° to 160° C. and recovering a distillate having a composition close to that of the respective azeotrope at said pressure $p_1$, b) expanding resultant distillate leaving the head of said first column to a pressure $p_2$ of 0.5 to 10 bars and lower than $p_1$ by a value $\Delta p$ of 0.5 to 12 bars, and c) introducing resultant expanded distillate into a second distillation column operating at said pressure $p_2$ and at a temperature ranging between a bottoms temperature of 60° to 150° C. and a head temperature of 50° to 130° C.

13. A process for the separation of tert. butyl ethyl ether (TBEE) from mixtures thereof with ethanol, said process comprising conducting a first distillation in a first distillation column operating under a pressure $p_1$, and recovering from said first distillation column a distillate having a composition of substantially an azeotropic composition of the tert. butyl ethyl ether and the ethanol at said pressure $p_1$; and passing resultant distillate to a second distillation column operating under a pressure $p_2$ which is lower than $p_1$ by a value of at least 0.5 bars, and recovering from said second distillation column, a distillate having a composition of substantially the azeotropic composition of the tert. butyl ether and the ethanol at said pressure $p_2$; and recycling the latter distillate to at least one of said first and second distillation columns.

* * * * *